United States Patent [19]
Jones

[11] Patent Number: 5,284,058
[45] Date of Patent: Feb. 8, 1994

[54] DUAL BEAM COMPLEX MODULUS APPARATUS

[75] Inventor: David I. G. Jones, Dayton, Ohio

[73] Assignee: The United States of America as represented by the Secretary of the Air Force, Washington, D.C.

[21] Appl. No.: 70,746

[22] Filed: Jun. 2, 1993

Related U.S. Application Data

[62] Division of Ser. No. 820,427, Jan. 8, 1992, Pat. No. 5,245,876.

[51] Int. Cl.⁵ ........................................... G01N 29/12
[52] U.S. Cl. ............................................................ 73/579
[58] Field of Search ................ 73/573, 579, 581, 594, 73/649, 651

[56] References Cited

U.S. PATENT DOCUMENTS

| | | | |
|---|---|---|---|
| Re. 29,288 | 7/1977 | Schilling, Jr. | 73/588 |
| 2,735,295 | 2/1956 | Piety | 73/763 |
| 3,319,460 | 5/1967 | Barigant | 73/579 |
| 3,610,027 | 10/1971 | Woboditsch | 73/579 |
| 3,751,977 | 8/1973 | Schilling, Jr. | 73/579 |
| 3,786,673 | 1/1974 | Weissmann | 73/579 |
| 3,901,074 | 8/1975 | Douglas | 73/579 |
| 3,903,734 | 9/1975 | Douglas | 73/579 |
| 4,034,602 | 7/1977 | Woo et al. | 73/579 |
| 4,170,141 | 10/1979 | Woo | 73/579 |
| 4,297,884 | 11/1981 | Leveque et al. | 73/579 |
| 4,412,452 | 11/1983 | Biot et al. | 73/579 |

Primary Examiner—John E. Chapman
Assistant Examiner—Rose M. Finley
Attorney, Agent, or Firm—Bobby D. Scearce; Thomas L. Kundert

[57] ABSTRACT

System and method for measuring complex shear or Young's modulus of a polymeric material are described wherein first and second beams of preselected lengths and different thicknesses are disposed in parallel spaced relationship firmly held at first ends thereof and first and second spaced gripping members are attached along the beams, a specimen of polymeric material is disposed between confronting surfaces of the gripping members, a time varying force is applied to one beam, the time varying displacements of the beams are measured, and the modulus of the polymeric material is calculated from the measurements.

5 Claims, 2 Drawing Sheets

DUAL BEAM COMPLEX MODULUS APPARATUS

RIGHTS OF THE GOVERNMENT

The invention described herein may be manufactured and used by or for the Government of the United States for all governmental purposes without the payment of any royalty.

This is a division of application Ser. No. 07/820,427 filed Jan. 8, 1992 now U.S. Pat. No. 5,245,876.

BACKGROUND OF THE INVENTION

The present invention relates generally to methods and systems for measuring physical properties of materials, and more particularly to a direct measurement system for determining the complex moduli of polymeric materials.

Methods for measuring complex moduli of polymeric damping materials generally are of two major types, namely, indirect resonant beam techniques and direct stiffness systems. The beam techniques are considered to be indirect because complex modulus values for the polymeric material are calculated, using appropriate formulae, from measurements of changes in modal damping and resonant frequency occurring in a beam of the polymeric material or in a beam coated with a polymer layer. Errors may arise because small differences between measurements on coated and uncoated beams may be magnified because of assumptions made in the mathematical treatment.

Direct measurement systems operate by applying an appropriate time varying force to a specimen of the polymeric material and calculating the complex modulus from a measured response to that force. The measurement chain is often quite long and consists of many finite mass and stiffness elements which are major sources of error, such as unwanted resonances in the desired frequency range or systematic under-estimation of true specimen stiffness when near the system stiffness. These disadvantages are difficult to overcome and direct stiffness measurement systems are best used for low to medium range measured modulus values.

The invention solves or substantially reduces in critical importance problems with prior art systems and methods as just described by providing system and method for measuring complex shear or Young's modulus of a polymeric material wherein first ends of two parallel beams of unequal thicknesses are attached to a base with a polymer specimen between the second ends, a time varying force is applied to one beam and the displacement responses of both beams are measured, with amplitude and phase angles determined by suitable displacement measuring sensors. The complex modulus of the polymer at the specific driving frequency and temperature is determined using an equation.

It is therefore a principal object of the invention to provide improved system and method for measuring physical properties of materials.

It is a further object of the invention to provide system and method for direct measurement of complex moduli of polymeric materials.

It is yet another object of the invention to provide system and method for direct measurement of shear or Young's modulus of polymeric materials over wide frequency and temperature ranges.

These and other objects of the invention will become apparent as a detailed description of representative embodiments proceeds.

SUMMARY OF THE INVENTION

In accordance with the foregoing principles and objects of the invention, system and method for measuring complex shear or Young's modulus of a polymeric material are described wherein first and second beams of preselected lengths and different thicknesses are disposed in parallel spaced relationship firmly held at first ends thereof and first and second spaced gripping members are attached along the beams, a specimen of polymeric material is disposed between confronting surfaces of the gripping members, a time varying force is applied to one beam, the time varying displacements of the beams are measured, and the modulus of the polymeric material is calculated from the measurements.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
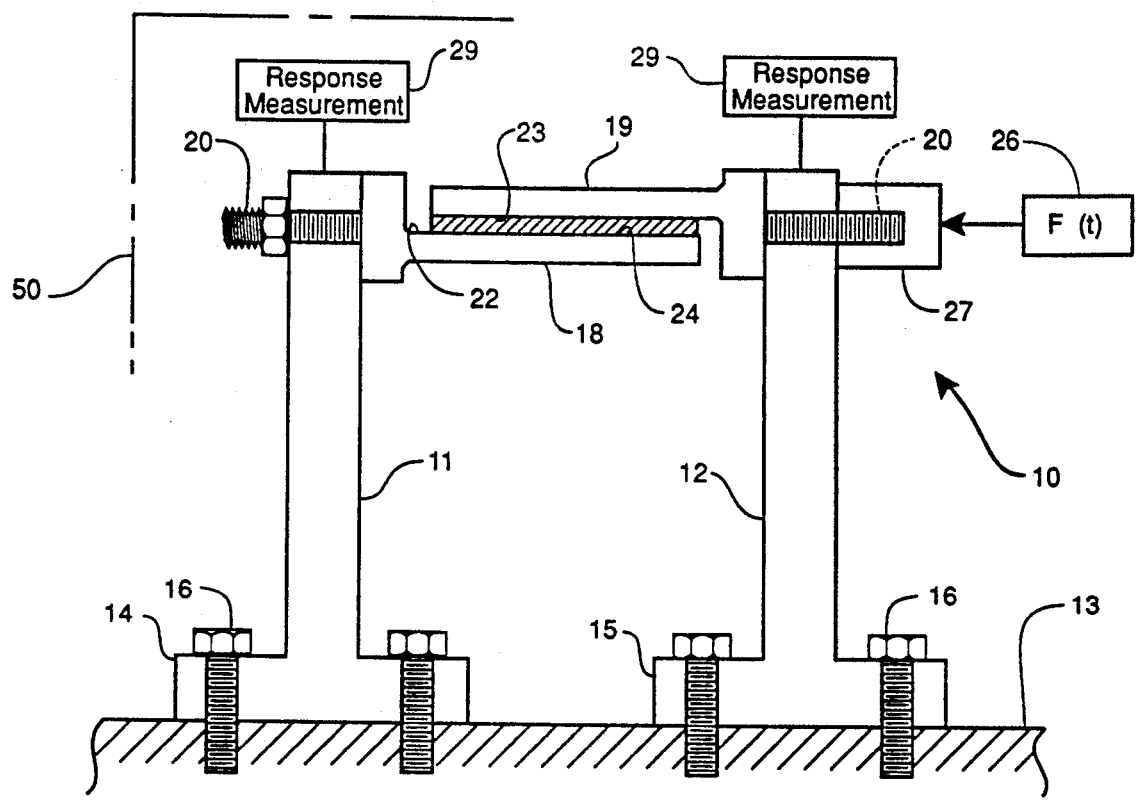
FIG. 1 is a sketch of a representative system of the invention and useful in the practice of the method thereof.

Referring now to FIG. 1, shown therein is a sketch of system 10 representative of the invention and useful in the practice of the method thereof. First and second beams 11, 12 of preselected length and different thicknesses are disposed in preselected (adjustable) parallel spaced relationship, each firmly supported at one (e.g. lower) end to a substantially stationary base 13 through means such as flanges 14, 15 and bolts 16. In the practical application of the method of the invention, beams 11, 12 may ordinarily have length in the range of from about 5 to 20 cm. Beams 11, 12 have different thicknesses in order to provide a corresponding preselected wide difference in stiffnesses therebetween. Accordingly, beams 11, 12 may comprise steel, aluminum, titanium, magnesium, or other suitable material; beam 11 will generally range in thickness from about 0.2 to 0.5 cm, and beam 12 will generally range in thickness from about 0.5 to 2.0 cm. Beams 11, 12 optimally will have thicknesses differing by a factor of about 2 to 30, and preferably about 5, so that a sufficiently wide range of specimen stiffnesses may be covered. A pair of substantially flat grip members 18, 19 are attached as through bolts 20 at respective upper ends of beams 11, 12, and are sized and configured to define space 22 therebetween for receiving a test specimen 23. It is noted that members 18, 19 may, in an alternative structure for the invention, be disposed anywhere along the length of beams 11, 12, which structure may provide certain versatility to measurement taking and specimen analysis utilizing the invention. Specimen 23 normally is in the form of a flat sheet of material held firmly between confronting surfaces of members 18, 19 using any suitable adhesive 24 as would occur to the skilled artisan guided by these teachings. Materials suitable for testing as specimen 23 in the practice of the invention include sheet materials such as silicone, urethane, acrylic, or similar polymer type materials. Specimen 23 thickness ordinarily ranges from about 0.1 to 5 mm. The FIG. 1 arrangement places specimen 23 in a configuration for testing in shear, although arrangements comprising grip members 18, 19 of other geometries placing the specimen in compression or tension may also be envisioned within the scope hereof by the skilled artisan practicing the invention. Time varying force generating means 26 (harmonic, non-harmonic, random or pulse) such as a piezoelectric or electrodynamic shaker, magnetic force transducer, impact hammer or other appropriate device acts through force gauge 27 in order to selectively vibrate beams 11, 12. The response of system 10 to force generating means 26 is measured by suitable measuring means 29, such as an optical vibrometer, capacitance, non-contact or eddy current transducer, laser velocimeter, accelerometer or the like, attached to or placed appropriately close to the tip (top) ends of beams 11, 12.

Figure 2:
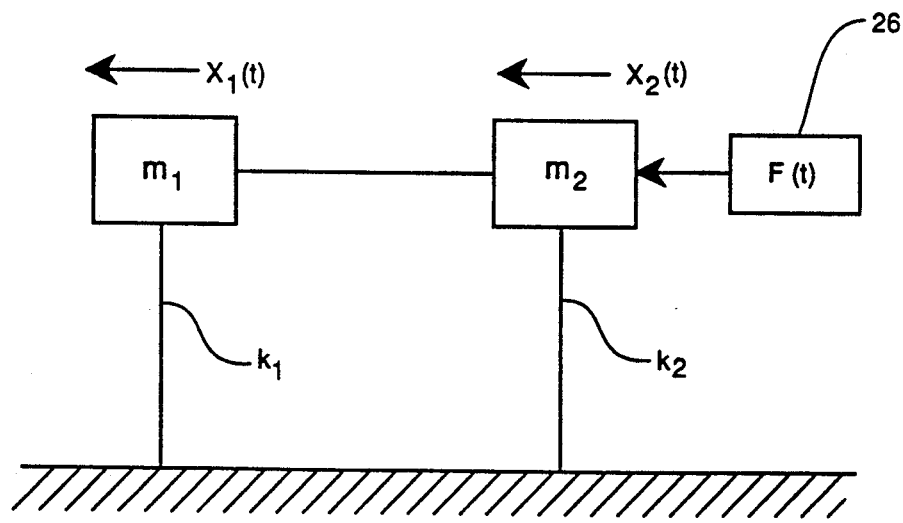
FIG. 2 is a simplified model of the FIG. 1 system.

Referring now to FIG. 2, shown therein is a simplified model of system 10 for illustrating responses to force generating means 26 in a determination of system parameters for measuring complex moduli of specimen 23. In FIG. 2, force generating means 26 acts with harmonic time-varying force F(t) upon effective masses $m_1, m_2$ supported, respectively, by stiffnesses $k_1, k_2$ representative of beams 11, 12 and connected by complex stiffness $k_s$ representative of specimen 23. Parameters $m_1, k_1, m_2, k_2$ may be determined from tests on system 10 absent specimen 23. The simple model shown in FIG. 2 is valid at frequencies as high as the first resonance frequency of the thinnest beam and as low as about zero Hz, although practical test times limit the lower frequency to about 1/1000 Hz. Elementary analysis applied to the FIG. 2 model shows that the complex stiffness $k_s(1+i\eta_s)$ of specimen 23 can be determined from measured harmonic responses $X_1(t)$ and $X_2(t)$ as follows:

$$k_s = (k_1 - m_1\omega^2)R(X_1/(X_1-X_2)) \quad (1)$$

$$\eta_s = I(X_1/(X_1 X_2))/R(X_1/(X_1-X_2)) \quad (2)$$

where $\eta_s$ is the loss factor of the specimen, and $\omega$ is the driving frequency of force generating means 26 in radians per second; R and I the in-phase and out-of-phase components of the system response and are evaluated from measured amplitudes $|X_1|$ and $|X_2|$ and phase angles $\phi_1$ and $\phi_2$ measured relative to the driving force signal $F(t)=F\exp(i\omega t)$, such that $X_1=|X_1|\exp(i\phi_1)$, $R(X_1)=|X_1|\cos(\phi_1)$, $I(X_1)=|X_1|\sin(\phi_1)$, etc. It then follows that, $$\frac{X_1}{X_1-X_2} = \frac{1}{1-\frac{|X_2|\exp(i\phi_2)}{|X_1|\exp(i\phi_1)}} = \frac{1}{1-\frac{|X_2|}{|X_1|}\{\cos(\phi_2-\phi_1)+i\sin(\phi_2-\phi_1)\}} \quad (3)$$

from which the in-phase and out-of-phase components are readily calculated using the theory of complex numbers, by one skilled in the art. At frequencies well below the first resonance of the system, $m_1\omega^2$ and $m_2\omega^2$ are small compared with $k_1$ or $k_2$ and Eq (1) may be simplified accordingly. The dynamic range of the system may be extended by making $k_1$ and $k_2$ differ by one, two or more orders of magnitude (stiffness is proportional to the cube of beam thickness), and repeating the tests by exciting first one beam and then the other so that $k_1$ and $k_2$ are switched (may be done without disturbing the specimen). For a dynamic range of 80 db (e.g. 1/100 to 100), values of $k_s$ may be measured within the range $k_1/100$ to $100k_1$. If $k_2=100k_1$, switching excitation locations gives $k_s$ within a range $k_1/100$ to $10000k_1$, and provides an effective dynamic range of 120 db. Measurements may be made over a wide, continuous, range of frequencies ranging from well below 1 Hz to 1000 Hz, as compared to a set of discrete frequencies characteristic of prior art (indirect/beam) techniques.

Figure 3:
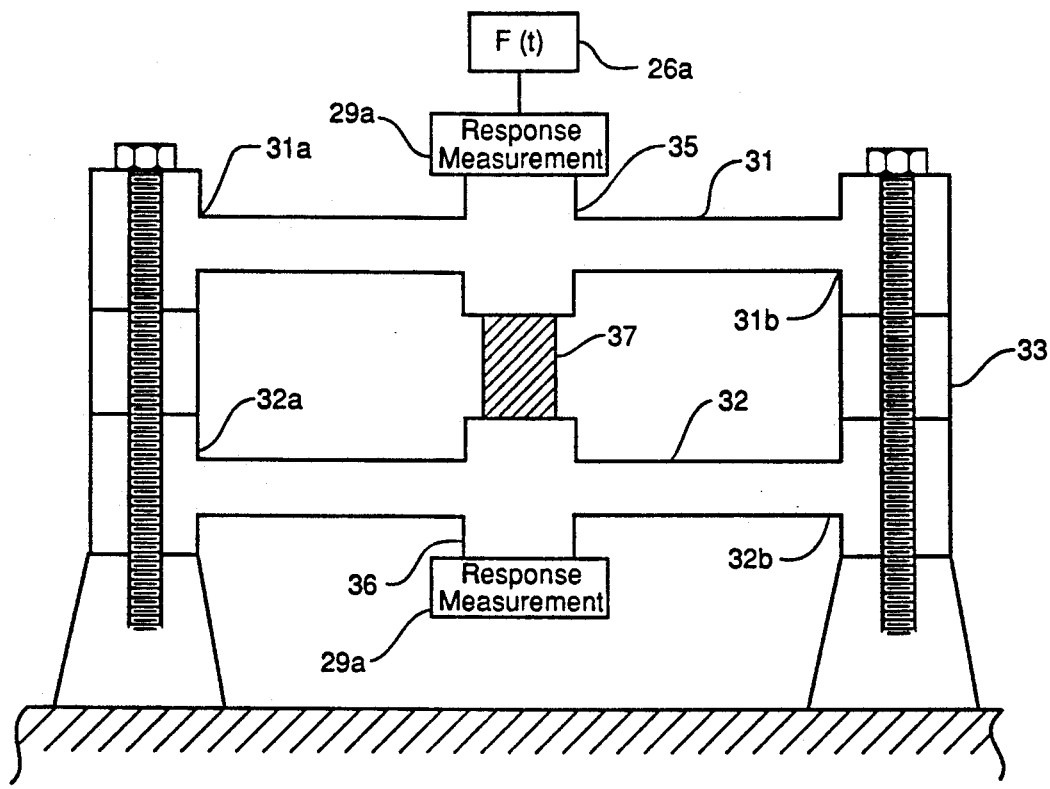
FIG. 3 shows an alternative arrangement for the invention comprising two beams each clamped at both ends.

Referring now to FIG. 3, shown therein is an alternative embodiment of the invention comprising two beams each clamped at both ends. In FIG. 3, various elements have functions similar to those of similarly named elements of the FIG. 1 embodiment. Beams 31, 32 are sized and have different thicknesses similarly to beams 11, 12 of the FIG. 1 system, but beams 31, 32 are each firmly held at both ends 31a, b, 32a, b to substantially stationary structure 33 in the parallel configuration suggested in FIG. 3. Gripping members 35, 36 are disposed along beams 31, 32 intermediate the ends thereof (preferably near the beam centers) in spaced relationship for supporting a specimen 37 therebetween for testing. In the FIG. 3 arrangement, specimen 37 is held in tension or compression, although, as in the FIG. 1 configuration, other arrangements and grip member geometries may be envisioned by the skilled artisan to place specimen 37 in shear. Specimen 37 may be of the general form and may be held between members 35, 36 similarly to specimen 23 of FIG. 1. Time varying force generating means 26a selectively vibrates beams 31, 32, and the response thereto of beams 31, 32 and specimen 37 is measured by measuring means 29a disposed on either side of beams 31, 32. Specimen 37 stiffness is then calculated from the measured responses using an analysis corresponding to that presented above.

Figure 4:
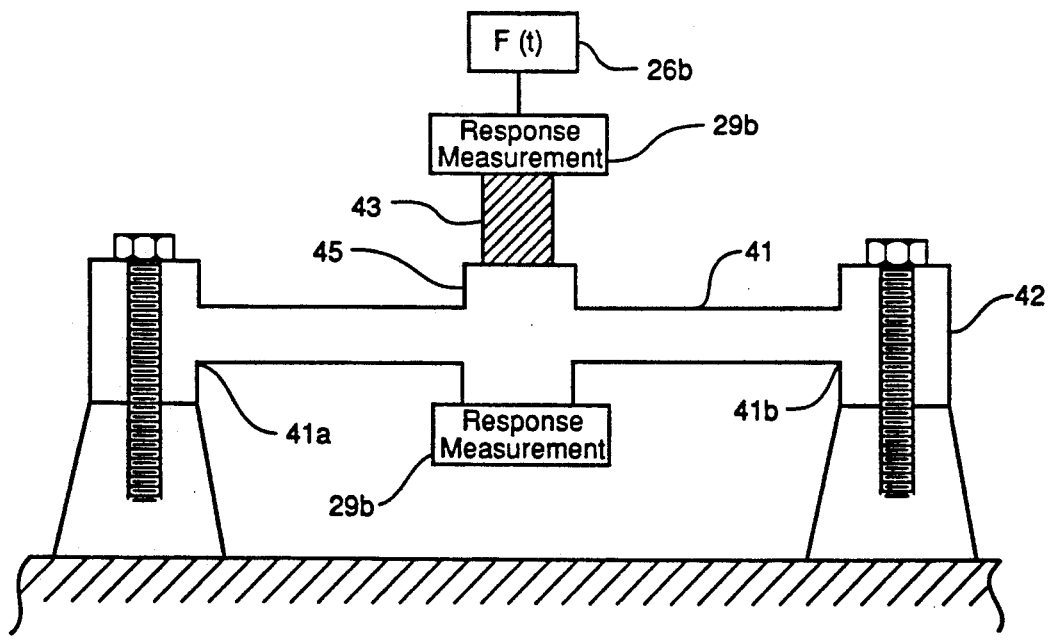
FIG. 4 shows a special case of the FIG. 3 embodiment comprising a single beam configuration.

Referring now to FIG. 4, shown therein is another embodiment of the invention utilizing a single beam 41 clamped at both ends 41a, b to stationary structure 42. In the analysis of the system shown in FIG. 4 and the measurements taken therefrom in characterizing a specimen, it is seen that the FIG. 4 system is essentially a special case of the FIG. 3 system wherein one of the beams has zero thickness and stiffness. Specimen 43 may be held between gripping member 45 and a surface of one response measuring means 29b element. Time varying force generating means 26b is disposed to act directly into specimen 43, and the response of beam 41 and specimen 43 is measured utilizing measuring means 29b elements. Specimen 43 stiffness may then be calculated as taught above considering zero stiffness of a second beam.

It is noted in addition to the foregoing, and with reference again to FIG. 1, that temperature dependence of specimen stiffness properties may be determined by disposing the system within a temperature controlled environment defined by enclosure 50, such as a furnace or refrigerator, as would occur to one skilled in the appropriate art guided by these teachings.

The invention therefore provides system and method for direct measurement of complex moduli of polymeric materials. It is understood that modifications to the invention may be made, as might occur to one skilled in the field of the invention, within the scope of the appended claims. All embodiments contemplated hereunder which achieve the objects of the invention have therefore not been shown in complete detail. Other embodiments may be developed without departing from the spirit of the invention or from the scope of the appended claims.

I claim:

1. A system for measuring complex shear or Young's modulus of a polymeric material, comprising:
    (a) a beam of preselected length and thickness firmly supported at a first end thereof;
    (b) a gripping member attached to said beam along the length thereof for attaching to said gripping member a specimen of polymeric material for measurement of said complex shear or Young's modulus of said material;
    (c) means for generating a time varying force operatively attached to one of said beam and said specimen;
    (d) means for operative attachment to at least one of said beam and said specimen for measuring time varying displacements of said beam; and
    (e) means for calculating said modulus of said material utilizing measurements of said time varying displacements.

2. The system of claim 1 wherein said beam is firmly supported at said first end and at a second end thereof and said gripping member is disposed along said beam intermediate said first and second ends.

3. The system of claim 1 wherein said beam comprises steel, aluminum, titanium or magnesium.

4. The system of claim 1 wherein said means for generating a time varying force is a piezoelectric shaker, electrodynamic shaker, magnetic force transducer or impulse hammer.

5. The system of claim 1 wherein said means for measuring time varying displacements is an optical vibrometer, capacitance transducer, non-contact transducer, eddy current transducer, laser velocimeter, or accelerometer.

* * * * *